US009963802B2

(12) United States Patent
Borst et al.

(10) Patent No.: US 9,963,802 B2
(45) Date of Patent: May 8, 2018

(54) METHOD OF DELINTING COTTON SEEDS

(71) Applicant: BASF SE, Ludwigshafen (DE)

(72) Inventors: Joseph P. Borst, Plymouth, MI (US); Kenneth L. Zack, Wyandotte, MI (US)

(73) Assignee: BASF SE, Ludwigshafen (DE)

( * ) Notice: Subject to any disclaimer, the term of this patent is extended or adjusted under 35 U.S.C. 154(b) by 71 days.

(21) Appl. No.: 15/123,498

(22) PCT Filed: Mar. 3, 2015

(86) PCT No.: PCT/US2015/018485
§ 371 (c)(1),
(2) Date: Sep. 2, 2016

(87) PCT Pub. No.: WO2015/134496
PCT Pub. Date: Sep. 11, 2015

(65) Prior Publication Data
US 2017/0073842 A1    Mar. 16, 2017

Related U.S. Application Data

(60) Provisional application No. 61/947,772, filed on Mar. 4, 2014.

(51) Int. Cl.
*D01C 1/00* (2006.01)
*D01G 9/02* (2006.01)
*A01N 25/00* (2006.01)
*A01N 25/30* (2006.01)

(52) U.S. Cl.
CPC ............. *D01C 1/00* (2013.01); *A01N 25/00* (2013.01); *D01G 9/02* (2013.01)

(58) Field of Classification Search
None
See application file for complete search history.

(56) References Cited

U.S. PATENT DOCUMENTS

| | | | | |
|---|---|---|---|---|
| 1,425,688 A * | 8/1922 | Polhamus | .................. | B02B 3/00 134/27 |
| 2,437,397 A * | 3/1948 | McLemore | ............... | B02B 3/00 26/4 |
| 2,618,103 A * | 11/1952 | Streets | ..................... | A01C 1/06 47/5 |
| 2,696,821 A | 12/1954 | Streets | | |
| 4,064,636 A | 12/1977 | Downing | | |
| 4,083,537 A | 4/1978 | Smith | | |
| 4,087,316 A | 5/1978 | Jividen et al. | | |
| 4,132,807 A | 1/1979 | Duke | | |
| 4,154,021 A | 5/1979 | Griffith et al. | | |
| 4,209,316 A * | 6/1980 | McDaniel | ............. | A01N 43/54 504/196 |
| 4,259,764 A | 4/1981 | Downing | | |
| 4,343,070 A | 8/1982 | Wade et al. | | |
| 4,371,449 A | 2/1983 | Smith, Jr. | | |
| 4,834,788 A * | 5/1989 | Young | .................... | A01N 59/02 504/125 |
| 5,249,335 A * | 10/1993 | Jones | ....................... | D01B 1/08 19/40 |
| 5,282,953 A * | 2/1994 | Gernon | .................... | C25D 3/32 106/1.05 |
| 5,363,754 A * | 11/1994 | Coles | ..................... | A23N 17/00 19/40 |
| 5,466,601 A | 11/1995 | Jenkins et al. | | |
| 5,632,116 A | 5/1997 | Dismuke, Jr. et al. | | |
| 5,638,634 A | 6/1997 | Wadlington | | |
| 5,750,466 A | 5/1998 | Wedegaertner et al. | | |
| 5,858,767 A | 6/1999 | Miettinen-Oinonen et al. | | |
| 6,531,629 B1 * | 3/2003 | Eiermann | ............ | C07C 303/16 562/118 |
| 7,179,362 B2 * | 2/2007 | Dietterle | ................... | C25D 3/58 205/241 |
| 7,666,816 B2 * | 2/2010 | Griffiths | ................. | A01N 25/04 504/348 |
| 2008/0161591 A1 * | 7/2008 | Richards | ................. | C01B 15/08 558/44 |
| 2008/0271295 A1 * | 11/2008 | Lightening | .............. | D01G 9/00 19/41 |
| 2011/0259367 A1 * | 10/2011 | Ahmed | ..................... | C11D 3/30 134/10 |
| 2012/0260938 A1 * | 10/2012 | Zack | ....................... | C02F 1/683 134/5 |
| 2013/0067690 A1 | 3/2013 | Wedegaertner et al. | | |
| 2016/0237170 A1 * | 8/2016 | Rittig | ...................... | C08H 8/00 |

FOREIGN PATENT DOCUMENTS

| | | |
|---|---|---|
| AU | 546527 B2 | 9/1985 |
| CA | 2 011 013 A1 | 8/1990 |
| CN | 1045136 A | 9/1990 |

(Continued)

OTHER PUBLICATIONS

International Search Report for Application No. PCT/US2015/018485 dated Jun. 18, 2015, 4 pages.
English language abstract not found for CN 1045136; however, see English language equivalent CA 2,011,013. Original document extracted from espacenet.com database on Sep. 21, 2016,16 pages.
English language abstract and machine-assisted English translation for CN 1065409 extracted from the espacenet.com database on Sep. 21, 2016, 8 pages.
English language abstract and machine-assisted English translation for CN 201536480 extracted from the espacenet.com database on Sep. 21, 2016, 6 pages.
English language abstract and machine-assisted English translation for CN 201536481 extracted from the espacenet.com database on Sep. 21, 2016, 7 pages.

(Continued)

*Primary Examiner* — Joseph D Anthony
(74) *Attorney, Agent, or Firm* — Armstrong Teasdale LLC

(57) ABSTRACT

A method of delinting cotton seeds with an alkanesulfonic acid comprises the steps of applying the alkanesulfonic acid to surfaces of linted cotton seeds, optionally heating the linted cotton seeds, and applying mechanical force to the surfaces of the linted cotton seeds. A composition for delinting cotton seeds comprises an alkanesulfonic acid (e.g. methanesulfonic acid (MSA)), a surfactant, and water.

13 Claims, No Drawings

(56) References Cited

FOREIGN PATENT DOCUMENTS

| | | |
|---|---|---|
| CN | 1065409 C | 5/2001 |
| CN | 201536480 U | 8/2010 |
| CN | 201536481 U | 8/2010 |
| CN | 201706861 U | 1/2011 |
| CN | 201797717 U | 4/2011 |
| CN | 201826205 U | 5/2011 |
| CN | 101584270 B | 9/2011 |
| CN | 101922854 B | 11/2011 |
| CN | 101911876 B | 8/2012 |
| CN | 102177777 B | 8/2012 |
| CN | 102668768 A | 9/2012 |
| CN | 102703394 A | 10/2012 |
| CN | 202635040 U | 1/2013 |
| CN | 202818917 U | 3/2013 |
| CN | 202823267 U | 3/2013 |
| GB | 1 501 164 A | 2/1978 |
| IN | 201168 B | 3/2007 |
| SU | 418573 A1 | 3/1974 |
| SU | 425993 A1 | 4/1974 |
| SU | 499348 A1 | 1/1976 |
| SU | 499350 A1 | 1/1976 |
| SU | 626127 A1 | 9/1978 |
| SU | 1119622 A1 | 10/1984 |
| SU | 1147775 A1 | 3/1985 |
| SU | 1283260 A1 | 1/1987 |
| SU | 1317037 A1 | 6/1987 |
| SU | 1615242 A1 | 12/1990 |
| WO | WO 94/23113 A1 | 10/1994 |
| WO | WO 96/09424 A1 | 3/1996 |
| WO | WO 02/083999 A1 | 10/2002 |

OTHER PUBLICATIONS

English language abstract and machine-assisted English translation for CN 201706861 extracted from the espacenet.com database on Sep. 21, 2016, 9 pages.
English language abstract and machine-assisted English translation for CN 201797717 extracted from the espacenet.com database on Sep. 21, 2016, 5 pages.
English language abstract and machine-assisted English translation for CN 201826205 extracted from the espacenet.com database on Sep. 21, 2016, 5 pages.
English language abstract and machine-assisted English translation for CN 101584270 extracted from the espacenet.com database on Sep. 21, 2016, 10 pages.
English language abstract and machine-assisted English translation for CN 101922854 extracted from the espacenet.com database on Sep. 21, 2016, 9 pages.
English language abstract and machine-assisted English translation for CN 101911876 extracted from the espacenet.com database on Sep. 21, 2016, 11 pages.
English language abstract and machine-assisted English translation for CN 102177777 extracted from the espacenet.com database on Sep. 21, 2016, 11 pages.
English language abstract and machine-assisted English translation for CN 102668768 extracted from the espacenet.com database on Sep. 21, 2016, 9 pages.
English language abstract and machine-assisted English translation for CN 102703394 extracted from the espacenet.com database on Sep. 21, 2016, 13 pages.
English language abstract and machine-assisted English translation for CN 202635040 extracted from the espacenet.com database on Sep. 21, 2016, 9 pages.
English language abstract and machine-assisted English translation for CN 202818917 extracted from the espacenet.com database on Sep. 21, 2016, 8 pages.
English language abstract and machine-assisted English translation for CN 202823267 extracted from the espacenet.com database on Sep. 21, 2016, 6 pages.
English language abstract and machine-assisted English translation for in 201166 extracted from IP India Services database on Sep. 21, 2016, 8 pages.
Machine-assisted English translation for SU 418573 extracted from the espacenet.com database on Sep. 21, 2016, 3 pages.
Machine-assisted English translation for SU 425993 extracted from the espacenet.com database on Sep. 21, 2016, 5 pages.
Machine-assisted English translation for SU 499348 extracted from the espacenet.com database on Sep. 21, 2016, 2 pages.
Machine-assisted English translation for SU 499350 extracted from the espacenet.com database on Sep. 21, 2016, 4 pages.
Machine-assisted English translation for SU 626127 extracted from the espacenet.com database on Sep. 21, 2016, 3 pages.
Machine-assisted English translation for SU 1119622 extracted from the espacenet.com database on Sep. 21, 2016, 5 pages.
Machine-assisted English translation for SU 1147775 extracted from the espacenet.com database on Sep. 21, 2016, 3 pages.
Machine-assisted English translation for SU 1283260 extracted from the espacenet.com database on Sep. 21, 2016, 4 pages.
Machine-assisted English translation for SU 1317037 extracted from the espacenet.com database on Sep. 21, 2016, 5 pages.
Machine-assisted English translation for SU 1615242 extracted from the espacenet.com database on Sep. 21, 2016, 8 pages.
BASF, "Lutensol XL Surfactants", Sep. 2005, 9 pages.
BASF, "Safety Data Sheet—Lutensol XL 70", Mar. 7, 2012, pp. 1-6.
Ryavalad, Shivayogi et al., "Effect of Acid Delinting Seed Treatment and Containers on Storability of Cotton Hybrid", Karnataka J. Agric. Sci. 22 (1), 2009, Pates 56-60.

\* cited by examiner

METHOD OF DELINTING COTTON SEEDS

CROSS-REFERENCE TO RELATED APPLICATIONS

This application is the National Stage of International Patent Application No. PCT/US2015/018485, filed on Mar. 3, 2015, which claims priority to and all the advantages of United States Provisional Patent Application No. 61/947,772, filed on Mar. 4, 2014, the content of which is incorporated herein by reference.

FIELD OF THE INVENTION

The present disclosure generally relates to a method of delinting cotton seeds and to a composition for delinting cotton seeds.

DESCRIPTION OF THE RELATED ART

Ginning processes remove impurities and waste (e.g. burs, dirt, stems, leaf material, etc.) from harvested cotton and yield cotton and cotton seeds. The cotton is used in textile and other applications, and the cotton seed is used for planting or is processed into cottonseed oil, meal, and hulls. However, before use in planting, the cotton seed is typically delinted in a delinting process.

The delinting process is required because a cotton seed separated in the ginning process typically has a residual covering of cotton, i.e., lint, attached to a hull of the cotton seed. This lint interferes with subsequent handling, processing, grading, and growing of the cotton seed. Conventional delinting processes include mechanical delinting processes which can be time-consuming and expensive and can even damage the cotton seed. Conventional delinting processes also include chemical delinting processes, especially when the intended use of the cotton seed is planting.

In a typical chemical delinting process, acid is applied to cotton seeds having lint thereon to 'degrade' the lint attached to the hulls. The cotton seeds are then heated, to accelerate the degradation of the lint by the acid. After heating, the linted cotton seeds are agitated, e.g. mixed in a rotating drum, to detach the covering of lint from the hull of the cotton seeds, and the delinted seeds are further processed to prepare them for distribution and planting.

Conventional chemical delinting processes utilize hydrochloric acid gas (HCl) or sulfuric acid ($H_2SO_4$) to 'degrade' the residual lint attached to the hulls of the cotton seeds. When hydrochloric acid and sulfuric acid are used in delinting processes, the corrosiveness of these acids, and in the case of HCl toxic vapors, pose handling and safety problems throughout the delinting processes. Further, the corrosiveness of hydrochloric acid and sulfuric acid damages equipment over time. In fact, sulfuric acid's oxidizing properties are especially strong and, when coupled with the thermal and mechanical stress which is placed on the cotton seeds during the delinting process, discolor the cotton seeds and may reduce seed germination rate (the likelihood that each seed will grow into a cotton plant). Furthermore, hydrochloric acid and sulfuric acid do not readily biodegrade, and thus also pose environmental concerns.

As such, there remains an opportunity to provide improved methods and compositions for delinting cotton seeds.

SUMMARY OF THE INVENTION AND ADVANTAGES

The present disclosure provides a method of delinting cotton seeds with an alkanesulfonic acid. The method comprises the step of applying the alkanesulfonic acid to surfaces of linted cotton seeds, optionally heating the linted cotton seeds, and applying mechanical force to the surfaces of the linted cotton seeds.

The present disclosure also provides a composition for delinting cotton seeds. The composition comprises the alkanesulfonic acid (e.g. methanesulfonic acid (MSA)), a surfactant, and water.

The method and the composition can be used to effectively remove lint attached to a hull of a cotton seed, i.e., delint a linted cotton seed. The alkanesulfonic acid is not as corrosive as acids traditionally used to delint cotton seeds, such as hydrochloric or sulfuric acid. As such, the composition is easier to handle and does not aggressively degrade equipment, discolor the hulls of the cotton seeds, and reduce seed germination rate. Further, the alkanesulfonic acid does not volatilize as readily as hydrochloric acid and does not cause the production of toxic and/or irritating vapors as sulfuric acid does during the process, making use of the method and the composition safer than conventional methods and compositions. Furthermore, the alkanesulfonic acid is readily biodegradeable and is thus environmentally friendly.

DETAILED DESCRIPTION OF THE INVENTION

The present disclosure provides a composition for delinting cotton seeds (i.e., removing lint from hulls of cotton seeds). The composition is particularly useful for replacing conventional compositions and vaporizations comprising acids (i.e. sulfuric and/or hydrochloric acids) traditionally used to delint cotton seeds.

The composition comprises the alkanesulfonic acid (e.g. methanesulfonic acid (MSA)), a surfactant, and water. However, the composition can be provided in various concentrations. As such, it is contemplated herein that the individual components of the composition can be included in the composition in various amounts. For example, a composition concentrate comprising the alkanesulfonic acid (e.g. MSA) and the surfactant with a minimal amount of or even no water, which can be diluted with water prior to use, is contemplated herein.

It is also contemplated herein that the composition can be supplied in two or more discreet components, which can be blended together prior to use. For example, the composition can be supplied in a two component system, with one component comprising the alkanesulfonic acid, and the other component comprising the surfactant, water, and other additives. In this example, the two components can be provided separately and blended together on site at the location of use just prior to use and, if desired, diluted with water.

The composition comprises an alkanesulfonic acid, such as MSA. Of course, the composition can comprise one or more types of the alkanesulfonic acid. The alkanesulfonic acid can be a short chain alkanesulfonic acid, such as one containing from 1 to 4 carbon atoms (e.g. one having propyl, ethyl, or methyl moieties). In one embodiment, the alkanesulfonic acid is para-toluene sulfonic acid. In another embodiment, the alkanesulfonic acid is isethionic acid or 2-hydroxyethanesulfonic acid. In a preferred embodiment, the alkanesulfonic acid is MSA.

In certain embodiments, the composition is substantially free to completely free of hydrochloric acid and/or sulfuric acid. These embodiments are useful to minimize the amount of corrosion to the surface of the system, as well as providing improved ease of handling of the composition. Typically, the composition is completely free of both of these acids.

Non-limiting examples of suitable alkanesulfonic acids, for purposes of the present disclosure, are commercially available from BASF Corporation of Florham Park, N.J., under the trade name LUTROPUR®, such as LUTROPUR® MSA and LUTROPUR® MSA 100. In certain embodiments, the MSA is one which is formed by an air oxidation process, rather than from a chlorooxidation process. As such, the MSA has less metal content, such as less than 1 mg/kg, and little to no chloro compounds, which are generally corrosive. Other non-limiting examples of suitable alkanesulfonic acids are described in U.S. Pat. No. 6,531,629 to Eiermann et al. and in U.S. Pat. App. Pub. No. 2008/0161591 to Richards, the disclosures of which are incorporated herein by reference in their entirety to the extent they do not conflict with the general scope of the present disclosure.

In a preferred embodiment, the alkanesulfonic acid comprises the MSA. The MSA is a strong organic acid that is believed to be completely non-oxidizing and thermally stable. In addition, MSA has a low vapor pressure, has no odor, and is biodegradable. As such, the MSA is easy to handle and environmentally friendly, especially in comparison to strong acids known in the art such as sulfuric acid, nitric acid, and hydrochloric acid.

MSA is soluble in water and has a pKa of −1.9, which is higher than the pKa of the first stage of dissociation sulfuric acid (−3 for the first stage of dissociation, 1.9 for the second stage of dissociation). MSA has a lower corrosivity in comparison to sulfuric acid, nitric acid, hydrochloric acid, and does not act as an oxidizing and/or dehydrating agent. Further, MSA is a significantly less strong sulfonation agent than sulfuric acid. To this end, it is believed that use of MSA minimizes the corrosion of processing equipment.

The alkanesulfonic acid, e.g. MSA, is typically present in the composition in an amount of from 2 to 50, alternatively from 4 to 35, alternatively from 6 to 25, alternatively from 8 to 20, parts by weight based on 100 parts by weight of the composition. The amount of alkanesulfonic acid present in the composition may vary outside of the ranges above, but is typically both whole and fractional values within these ranges. Further, it is to be appreciated that the composition may include a combination of different alkanesulfonic acids; in such a case, the total amount of all alkanesulfonic acids included in the composition is typically within the ranges above.

As set forth above, the composition also comprises the surfactant. If employed, the surfactant component is typically selected from the group of nonionic surfactants, anionic surfactants, cationic surfactants, amphoteric surfactants, and other ionic surfactants. It is to be appreciated that other types of surfactants can also be used.

In various embodiments, the surfactant comprises a non-ionic surfactant, or is a non-ionic surfactant. When used in conjunction with the alkanesulfonic acid, it is believed that the non-ionic surfactant helps accelerate the degradation or breakdown of the lint (cellulose) which is attached to the hulls of the linted cotton seeds by facilitating the wet-out of the composition on the lint. Once the lint is brought into contact with the composition, i.e., is wet-out, the alkanesulfonic acid works to quickly 'degrade' the lint.

Non-ionic surfactants, suitable for purposes of the present disclosure, include alcohol alkoxylates. Suitable alcohol alkoxylates include linear alcohol ethoxylates. Additional alcohol alkoxylates include alkylphenol ethoxylates, branched alcohol ethoxylates, secondary alcohol ethoxylates, castor oil ethoxylates, alkylamine ethoxylates (also known as alkoxylated alkyl amines), tallow amine ethoxylates, fatty acid ethoxylates, sorbital oleate ethoxylates, end-capped ethoxylates, or combinations thereof. Further non-ionic surfactants include amides such as fatty alkanolamides, alkyldiethanolamides, coconut diethanolamide, lauramide diethanolamide, cocoamide diethanolamide, polyethylene glycol cocoamide, oleic diethanolamide, or combinations thereof. Yet further non-ionic surfactants include polyalkoxylated aliphatic base, polyalkoxylated amide, glycol esters, glycerol esters, amine oxides, phosphate esters, alcohol phosphate, fatty triglycerides, fatty triglyceride esters, alkyl ether phosphate, alkyl esters, alkyl phenol ethoxylate phosphate esters, alkyl polysaccharides, block copolymers, alkyl polyglucocides, or combinations thereof.

In one embodiment, the non-ionic surfactant comprises an alcohol alkoxylate. In one specific embodiment, the non-ionic surfactant comprises an alcohol ethoxylate having the formula:

wherein R is a C6 to C24, alternatively a C6 to C20, alternatively a C8 to C18 alkyl group, and X is from 2 to 24, alternatively from 2 to 20, alternatively from 4 to 16.

Non-ionic surfactants, also suitable for purposes of the present disclosure, include polyalkylene oxide surfactants (also known as polyoxyalkylene surfactants or polyalkylene glycol surfactants). Suitable polyalkylene oxide surfactants include polyoxypropylene surfactants and polyoxyethylene glycol surfactants. Suitable surfactants of this type are synthetic organic polyoxypropylene (PO)-polyoxyethylene (EO) block copolymers. These surfactants generally comprise a di-block polymer comprising an EO block and a PO block, a center block of polyoxypropylene units (PO), and having blocks of polyoxyethylene grafted onto the polyoxypropylene unit or a center block of EO with attached PO blocks. Further, this surfactant can have further blocks of either polyoxyethylene or polyoxypropylene in the molecules. The surfactant may also include butylene oxide (BO) blocks, and can include random incorporations of two or three alkylene oxides, e.g. EO/PO/BO, EO/PO/PO, EO/EO/PO, etc. Such surfactants may be referred to in the art as "heteric" block surfactants.

Non-limiting examples of suitable non-ionic surfactants, for purposes of the present disclosure, are commercially available from BASF Corporation, under the trade names of PLURAFAC®; PLURONIC®; TETRONIC®; LUTROPUR®; LUTENSOL®, such as LUTENSOL® XL 70.

The surfactant is typically present in the composition in an amount of from 0.1 to 5, alternatively from 0.2 to 4, alternatively from 0.3 to 3, alternatively from 0.5 to 3, alternatively 0.5 to 2.5, parts by weight based on 100 parts by weight of the composition. The amount of the surfactant present in the composition may vary outside of the ranges above, but is typically both whole and fractional values within these ranges. Further, it is to be appreciated that the composition may include a combination of surfactants; in such a case, the total amount of all surfactants included in the composition is typically within the ranges above.

As alluded to above, it is believed that use of the surfactant in combination with the alkanesulfonic acid provides a synergistic effect on the delinting process. Typically, the ratio of the alkanesulfonic acid to the surfactant, by weight, in the composition is from 120:1 to 4:1, alternatively from 20:1 to 4:1, alternatively from 15:1 to 6:1, alternatively from 10:1 to 6:1.

The composition further comprises water, such that the alkanesulfonic acid and the surfactant are diluted, i.e., such that the composition is aqueous. The water can be of various types. In certain embodiments, the water is de-mineralized and/or de-ionized. The water is present in the composition in various amounts, depending on the embodiment. The water can be added to the composition as a separate component. However, it is to be appreciated that some of the water can also be imparted by the components of the composition, such as by the alkanesulfonic acid, when aqueous.

In certain embodiments, water is present in the composition in an amount of at least 30, alternatively at least 50, alternatively at least 70, alternatively at least 75, alternatively at least 80, alternatively at least 85, alternatively at least 90, parts by weight based on 100 parts by weight of the composition. The amount of water present in the composition may vary outside of the ranges above, but is typically both whole and fractional values within these ranges.

The composition can optionally comprise a corrosion inhibitor. A corrosion inhibitor may be defined, in general terms, as a substance that, when added to the composition, reduces the corrosion rate of a metal exposed to the composition. To this end, the corrosion inhibitor is useful for inhibiting corrosion of the surface of the equipment used in the delinting processes.

In one embodiment, the composition comprises an amphoteric surfactant which acts as both a corrosion inhibitor and a surfactant.

The composition can include any corrosion inhibitor known in the art. Of course, the composition can include more than one corrosion inhibitor, i.e., a combination of different corrosion inhibitors. Non-limiting examples of suitable corrosion inhibitors, for purposes of the present disclosure, are commercially available from BASF Corporation under the trade names of KORANTIN® (e.g. KORANTIN® BH, PM, MAT, PAT, and PP), GOLPANOL®, and LUGALVAN® (e.g. LUGALVAN® HS-1000).

In one embodiment, the corrosion inhibitor comprises an amphoteric surfactant. As such, the corrosion inhibitor may be the amphoteric surfactant or may include one or more additional components, such as water. If the corrosion inhibitor includes water, the amphoteric surfactant can be provided in various concentrations.

Suitable amphoteric surfactants, for purposes of the present disclosure, include betaines, imidazolines, and propionates. Further examples of suitable amphoteric surfactants include sultaines, amphopropionates, amphrodipropionates, aminopropionates, aminodipropionates, amphoacetates, amphodiacetates, and amphohydroxypropylsulfonates. In certain embodiments, the amphoteric surfactant is at least one of a propionate or an amphodiacetate. Further specific examples of suitable amphoteric surfactants include N-acylamino acids such as N-alkylaminoacetates and disodium cocoamphodiacetate, and amine oxides such as stearamine oxide. In one embodiment, the amphoteric surfactant comprises disodium cocoamphodiacetate.

In certain embodiments, the amphoteric surfactant is illustrated by the formulas: $RCH_2NHCH_2CH_2COOM$ or $RCH_2N(CH_2CH_2COOM)_2$, wherein M is a salt-forming cation (e.g. Na or H) and R is the hydrocarbon moiety of the long-chain fatty acid RCOOH, e.g. a $C_7$ to $C_{35}$, or a $C_7$ to $C_{18}$, fatty acid. Such amphoteric surfactants include sodium N-coco-β-aminopropionate, N-coco-β amino propionic acid; N-lauryl, myristyl-β-amino propionic acid; disodium N-tallow-β-iminopropionate; disodium N-lauryl-β-imino-propionate (also known as sodium lauriminodipropionate); and the partial sodium salt of N-lauryl-β-iminopropionic acid. In one embodiment, the amphoteric surfactant comprises sodium lauriminodipropionate.

As alluded to above, in certain embodiments, the corrosion inhibitor is aqueous. If the corrosion inhibitor is aqueous, the amphoteric surfactant is typically present in an amount of from 15 to 95, or 20 to 80, or 25 to 60, or 30 to 50, parts by weight, each based on 100 parts by weight of the corrosion inhibitor.

Non-limiting examples of suitable amphoteric surfactants, for purposes of the present disclosure, are available from BASF Corporation, under the trade names of DERIPHAT®, such as DERIPHAT® 160C; MAFO®, such as MAFO® 13 MOD 1; and DEHYTON®, such as DEHYTON® DC. It is to be appreciated that the corrosion inhibitor may include a combination of two or more different amphoteric surfactants.

If included, the corrosion inhibitor is typically present in the composition in an amount of from 0.02 to 2, alternatively from 0.05 to 1.5, alternatively from 0.1 to 1, parts by weight based on 100 parts by weight of the composition. The amount of the corrosion inhibitor present in the composition may vary outside of the ranges above, but is typically both whole and fractional values within these ranges. Further, it is to be appreciated that the corrosion inhibitor may include a combination of amphoteric surfactants and other components; in such a case, the total amount of all amphoteric surfactants and other components (excluding water) included in the composition is typically within the ranges above.

The composition can also optionally include a defoamer. The composition can include any defoamer known in the art. Of course, the composition can include more than one defoamer, i.e., a combination of different defoamers. If included, the defoamer is typically present in the composition in an amount of from 0.02 to 2, alternatively from 0.05 to 1.5, alternatively from 0.1 to 1, parts by weight based on 100 parts by weight of the composition. The amount of the defoamer present in the composition may vary outside of the ranges above, but is typically both whole and fractional values within these ranges. Further, it is to be appreciated that the defoamer may include a combination of defoamers; in such a case, the total amount of all defoamers included in the composition is typically within the ranges above.

Examples of suitable defoamers include silicone based defoamers and non-ionic block copolymers. If utilized, the defoamer is typically present in an amount of from 0.0005 to 1, 0.001 to 0.005, or 0.001 to 0.05, wt. %, each based on 100 parts by weight of the composition. Specific examples of suitable defoamers are commercially available from Dow Corning Corporation of Midland, Mich., under the trade name ANTIFOAM®, such as ANTIFOAM® 1430. Other specific examples include those commercially available from a variety of suppliers under the trade name FOAM BAN®, such as FOAM BAN® 149.

In certain embodiments, the composition further comprises one or more additives. Various types of additives can be used. Examples of suitable additives include colorants, antioxidants, dispersants, stabilizers, viscosity modifiers, and combinations thereof. If utilized, the additive(s) may be used in various amounts. For example, the additive(s) can be present in an amount of from 0 to 5, alternatively from 0.0005 to 5, alternatively from 0.0005 to 2.5, parts by weight based on 100 parts by weight of the composition.

In specific embodiments, the composition comprises MSA, the non-ionic surfactant, and water, and in further embodiments, consists essentially of MSA, the non-ionic surfactant, and water. In other specific embodiments, the composition comprises MSA, an alcohol ethoxylate having the formula $RO(CH_2CH_2O)_xH$ (wherein R is a $C_6$ to $C_{20}$ alkyl group and x is from 2 to 20), and water, and in further embodiments, consists essentially of MSA, an alcohol ethoxylate having the formula $RO(CH_2CH_2O)_xH$ (wherein R is a $C_6$ to $C_{20}$ alkyl group and x is from 2 to 20), and water. In yet other embodiments, the composition comprises MSA, an alcohol ethoxylate having the formula $RO(CH_2CH_2O)_xH$ (wherein R is a $C_6$ to $C_{20}$ alkyl group and x is from 2 to 20), a corrosion inhibitor comprising an amphoteric surfactant, and water, and in further embodiments, consists essentially of MSA, an alcohol ethoxylate having the formula $RO(CH_2CH_2O)_xH$ (wherein R is a $C_6$ to $C_{20}$ alkyl group and x is from 2 to 20), a corrosion inhibitor comprising an amphoteric surfactant, and water.

The composition typically has a pH of from −1.5 to 3, or −1 to 3, or −1 to 1, or 0 to 3, or 0 to 2, or 0 to 1, or 0.1 to 1, or 0.25 to 0.75, or 0.5 to 0.6. The pH of the composition is imparted by the type and amount of components employed to form the composition. For example, if the composition is diluted with water, the pH will generally increase.

The present disclosure also provides a method of delinting cotton seeds with an alkanesulfonic acid. The method comprises the steps of applying the alkanesulfonic acid to surfaces of linted cotton seeds, optionally heating the linted cotton seeds, and applying mechanical force to the surfaces of the linted cotton seeds. In a typical embodiment, the step of heating the linted cotton seeds is conducted subsequent to the step of applying the alkanesulfonic acid, and the step of applying mechanical force is conducted subsequent to the step of heating the linted cotton seeds.

The steps can be conducted in-line, as part of a continuous process. Alternatively, the steps can be conducted discretely, one step at a time, with various amounts of time between each step. Typically, the steps of the method are conducted in-line. The steps of the method can be conducted with/in multiple vessels, conveyors, etc. Alternatively, the entire method can be conducted in a single vessel.

In one embodiment, the alkanesulfonic acid (as is described above) is applied to the surfaces of linted cotton seeds as part of the composition set forth above. The method is particularly useful for replacing conventional compositions and vaporizations comprising acids (i.e. sulfuric and/or hydrochloric acids) traditionally used to delint cotton seeds.

The alkanesulfonic acid (or in some embodiments the composition) can be applied to the surface of the linted cotton seeds by various methods, such as by applying the alkanesulfonic acid to the surface (e.g. by dipping the linted cotton seeds in the alkanesulfonic acid), spraying the alkanesulfonic acid onto the linted cotton seeds surface, etc. Various application apparatuses understood in the art can be employed, such as a spraying apparatus, a dip tank, etc. In a preferred embodiment, the alkanesulfonic acid is sprayed on the linted cotton seeds. In yet another preferred embodiment, the linted cotton seed is soaked in the alkanesulfonic acid. Of course, in one embodiment, the step of applying the alkanesulfonic acid to the surface of linted cotton seeds is further defined as applying the composition described above, which comprises the alkanesulfonic acid, the surfactant, and water, to the surface of linted cotton seeds.

Further, it should be appreciated that the alkanesulfonic acid (or in some embodiments the composition) can be applied to the surface of the linted cotton seeds in a single step or in multiple sub-steps. For example, when the alkanesulfonic acid (or in some embodiments the composition) is applied to the surface of the linted cotton seeds via spraying, the linted cotton seeds can be sprayed with the alkanesulfonic acid a first time, and then sprayed with the with the alkanesulfonic acid a second time, with various intermediate steps contemplated as well, such as aging, heating, etc. As another example, the alkanesulfonic acid can be first applied to the surface of the linted cotton seeds via mixing the linted cotton seeds with the alkanesulfonic acid in a dip/mix tank and then applied a second time via spraying the alkanesulfonic acid on the linted cotton seeds, or vice versa.

In a preferred embodiment, the alkanesulfonic acid (or in some embodiments the composition) is applied to the surface of the linted cotton seeds via spraying at a rate of from 5 to 60, alternatively from 10 to 40, g/100 g of linted seeds. Obviously, the amount applied can vary outside of the ranges above depending on the concentration of the alkanesulfonic acid applied.

As discussed herein 'a surface of the linted cotton seed' is defined as the lint attached to, as well as an outer surface of, the hull of the linted cotton seed. Typically, the linted cotton seeds do not need to be pretreated, e.g. mechanically trimmed, rinsed with water, heated, etc. However, such pretreatment steps may be employed to expedite removal of the lint from the linted cotton seeds and speed up the delinting process.

For example, the method may further comprise the step of heating the alkanesulfonic acid (or in some embodiments the composition) and/or the linted cotton seeds prior to the step of applying the alkanesulfonic acid to surfaces of linted cotton seeds. Applying heat to the alkanesulfonic acid and/or the linted cotton seeds prior to, during, and/or subsequent to the step of applying the alkanesulfonic acid to surfaces of linted cotton seeds generally accelerates the delinting process. However, it is to be appreciated that the alkanesulfonic acid may also be applied to the surfaces of linted cotton seeds at ambient temperatures, e.g. temperatures typical of cotton ginning and cotton seed processing plants.

The method typically comprises the step of heating the linted cotton seeds. The linted cotton seeds are typically heated subsequent to the step of applying the alkanesulfonic acid to the surfaces of the linted cotton seeds. The step of heating the linted cotton seeds typically removes water from the linted cotton seeds. The linted cotton seeds can be heated by various methods, such as by exposing the linted cotton seeds to flame, to elevated air temperatures, to infra-red radiation, etc. Various application apparatuses understood in the art can be employed to heat the linted cotton seeds such as seed flaming apparatuses, forced air ovens, etc. In a preferred embodiment, the step of heating is conducted via exposure to elevated air temperatures in a forced air oven (or series of forced air ovens).

In various embodiments of the method, the temperature of the linted cotton seeds does not exceed 150, alternatively 145, ° F. during the step of heating the linted cotton seeds, or throughout the method for that matter. However, it should be appreciated that the temperatures in the previous sentence refer to the temperature of the hull of the linted cotton seed and that the step of heating the linted cotton seeds can also be further defined as exposing the linted cotton seed to air temperatures of greater than 150° F.

Further, it should be appreciated that the step of heating can include a single step or multiple sub-steps. For example, in various embodiments, the linted seeds can be heated before the step of applying the alkanesulfonic acid, during the step of applying the alkanesulfonic acid, alkanesulfonic acid, inbetween the steps of applying the alkanesulfonic acid and applying mechanical force, during the step of applying mechanical force, and/or after the step of applying mechanical force.

When the step of heating the linted cotton seeds is conducted subsequent to the step of applying the alkanesulfonic acid to the surfaces of the linted cotton seeds, the alkanesulfonic acid should be allowed to contact the surfaces of linted cotton seeds for a least a period of time (exposed to/aged) before drying. For example, the alkanesulfonic acid can be kept in contact for a period of time of from 1 to 60, alternatively from 1 to 50, alternatively 1 to 40, alternatively 1 to 30, alternatively from 1 to 20, alternatively from 1 to 10, minutes.

As set forth above, the method also comprises the step of applying mechanical force to the surfaces of the linted cotton seeds. The step of applying mechanical force is typically conducted subsequent to the steps of applying the alkanesulfonic acid and the step of heating. Mechanical force can be applied to the surfaces of the linted cotton seeds by various methods, such as by exposing the linted seeds to blown air, tumbling the linted seeds in a rotating vessel, etc. Various application apparatuses understood in the art can be employed to apply mechanical force to the linted cotton seeds. In a preferred embodiment, the linted cotton seeds are mixing in a rotating vessel, such as a baffled drum.

In various embodiments, the method further comprises the step of applying an acidity modifier to the delinted cotton seeds to adjust the acidity of the delinted cotton seeds. An acidity modifier is any substance that changes the pH of the delinted cotton seeds. Examples of the acidity modifier include calcium carbonate ("$CaCO_3$"), various weak bases, etc. In a preferred embodiment, calcium carbonate is applied in an amount sufficient to adjust the pH of the cotton seed to greater than 2, alternatively greater than 3, alternatively greater than 3.5, alternatively greater than 4, alternatively 5 (e.g. from 4 to 6). In one such embodiment, from 10 to 50, alternatively from 10 to 20, ounces of calcium carbonate are applied per 100 pounds of delinted seeds.

The method of the subject disclosure typically yields cotton seeds having an Initial pH (without use of an acidity modifier such as $CaCO_3$) of greater than 2, alternatively greater than 2.5, alternatively greater than 3, alternatively greater than 5 (e.g. from 4 to 6); a Final pH of greater than 3, alternatively greater than 3.5, alternatively greater than 4, alternatively greater than 5 (e.g. from 4.5 to 5.5) when treated with an acidity modifier such as $CaCO_3$); a free fatty acid value (FFA) of from 0.05 to 0.70, alternatively from 0.1 to 0.5, g/100 g. To test pH, a water solution is obtained from the addition of 50 g delinted cotton seed mixed with 100 mL of deionized water and the pH of the water solution is measured in accordance with pH testing procedures known in the art that is obtained from the addition of delinted cotton seed mixed with deionized water in a weight (g, cotton seed) to volume (mL water) ratio of 1 to 2. The method for determining the % FFA in cotton seed is AOCS Official Method Aa 6-38.

In one embodiment, the method yields cotton seeds having an Initial pH (without use of an acidity modifier such as $CaCO_3$) of greater than 2, and a Final pH of greater than 3.5 when treated with equal to or less than 6 oz of $CaCO_3$ per 100 lbs of delinted cotton seeds.

In another embodiment, the method utilizes a composition comprising alkanesulfonic acid in a concentration of between 10 and 14, alternatively between 11 and 13% and yields cotton seeds having an Initial pH (without use of an acidity modifier such as $CaCO_3$) of greater than 2.

Further, the method typically yields delinted cotton seeds having a germination rate at 86° F. of greater than 80%, alternatively greater than 90%, alternatively greater than 95%, alternatively greater than 98%; a germination rate at 81.5° F. of greater than 80%, alternatively greater than 90%, alternatively greater than 95%, alternatively greater than 98%; and a germination rate at 65° F. of greater than 60%, alternatively greater than 70%, alternatively greater than 80%. To test seed germination rate, a Petri dish is lined with a piece of Whatman #3 cellulose 6 μm filter paper, 10 delinted cotton seeds are placed on the filter paper, another sheet of the filter paper is placed on top of the delinted cotton seeds, and the filter paper is wet with 6 grams of DI water. The Petri dish and its contents are then incubated at 81.5° F. (27.5° C.) (or whatever temperature desired 86° F., 65° F., etc.) for 24 hours. After 24 hours, 2 more grams of water are added to the Petri dish, and the Petri dish and its contents are incubated at 81.5° F. (27.5° C.) (or whatever temperature desired 86° F., 65° F., etc.) for another 48 hours. If hypocotyl and radical development occurs, the seed is deemed to have germinated.

The following examples, illustrating the composition and method of the present disclosure, are intended to illustrate and not to limit the disclosure.

EXAMPLES

Examples 1 and 2

Examples 1 and 2 are lab-scale delinting experiments which generally require a greater concentration of acid than production-scale processes. As such, the Examples 1 and 2 and Comparative Examples 1 and 2 utilize concentrated MSA and sulfuric acid.

Comparison of MSA and Sulfuric Acid

The germination rates of cotton seeds delinted with MSA and sulfuric acid herein are based on the test method disclosed in J. Agric. Sci. 22(4): (896-897) 2009 (100 mL conc. sulfuric acid per kg of linted seed.)

Seed Examples 1 and 2 are formed according to the method of the subject application. Seed Example 1 is formed by adding 15 g. of linted seed to 2.6 g concentrated MSA (>99.8%) and stirred by hand at room temperature for 10 min, and Comparative Seed Example 1 is formed by adding 15 g. of linted seed to 2.8 g of concentrated sulfuric acid (96%) and stirred by hand at room temperature for 10 min. After 10 min. of stirring, Seed Example 1 and Comparative Seed Example 1 are rinsed with 100 mL of DI water and decanted, this rinsing process is repeated four times. The seed is then dried for 1 hr. at 131° F. (55° C.)

To form Seed Example 2 and Comparative Seed Example 2, the linted seed and the acids used in the process described in the preceding paragraph are separately heated for 1 hour at 131° F. (55° C.), followed by immediately combining and stirring to achieve delinting.

Seed Examples 1 and 2 and Comparative Seed Examples 1 and 2 are tested for weight loss, change in color, and germination rate, and the results are set forth in Table 1 below.

TABLE 1

| | Seed Example 1 | Comparative Seed Example 1 | Seed Example 2 | Comparative Seed Example 2 |
|---|---|---|---|---|
| Weight Loss (weight %) | 7.3 | 10.0 | 9.4 | 12.4 |
| Discoloration (visual observations) | No Color Change | Color Darkened to a Reddish-Brown Color | No Color Change | Color Darkened to a Reddish-Brown Color |
| Seed Germination Rate (%)* at 81.5° F. and Observations | — | — | 100% (hypocotyl was thicker and healthier than those of Comparative Seed Example 2) | 90% |
| Hypocotyl Length (mm) at 86° F. Germination Temperature | — | — | 17 | 14 |

To test seed germination rate, a Petri dish is lined with a piece of Whatman #3 cellulose 6 μm filter paper, 10 delinted cotton seeds are placed on the filter paper, another sheet of the filter paper is placed on top of the delinted cotton seeds, and the filter paper is wet with 6 grams of DI water. The Petri dish and its contents are then incubated at 81.5° F. (27.5° C.) or alternatively at 86° F. (30° C.) for 24 hours. After 24 hours, 2 more grams of water are added to the Petri dish, and the Petri dish and its contents are incubated at 81.5° F. (27.5° C.) or alternatively at 86° F. (30° C.) for another 48 hours. If hypocotyl and radical development occurs, the seed is deemed to have germinated.

Referring now to Table 1, Seed Examples 1 and 2 are not as discolored as Comparative Seed Examples 1 and 2. Further, Seed Example 2 exhibited higher germination rates and more robust seed growth and hypocotyl length than Comparative Seed Examples 2.

Example 3

Example 3 is a production-scale delinting trial. Seed Example 3 is formed according to the method of the subject application. The production-scale delinting trial of Example 3 is completed in a cotton seed delinting facility. Seed Example 3 is formed by treating 2000 lbs of linted seed with MSA (12% concentration). Once treated, Seed Example 3 is agitated and dried. Once dried, Seed Example 3 is treated with $CaCO_3$.

Comparative Seed Example 3 is formed by treating linted seed with sulfuric acid (10% concentration). Once treated, Comparative Seed Example 3 is agitated and dried. Once dried, Comparative Seed Example 3 is treated with $CaCO_3$.

Seed Example 3 and Comparative Seed Example 3 are tested for pH weight loss, change in color, and germination rate, and the results are set forth in Table 2 below.

TABLE 2

| | Seed Example 3 | Comparative Seed Example 3 |
|---|---|---|
| Delinting Observations | Final Seed Fully Delinted | Final Seed Fully Delinted |
| Initial pH (untreated seed) | 2.1 | 1.7 |

TABLE 2-continued

| | Seed Example 3 | Comparative Seed Example 3 |
|---|---|---|
| Final pH (6 oz $CaCO_3$ per 100 lbs of seed) | 3.9 | 1.8 |
| Final pH (8 oz $CaCO_3$ per 100 lbs of seed) | 5.0 | 3.5 |
| Seed Germination | Good (with 6 oz $CaCO_3$ per 100 lbs of seed) | Good (with 8 oz $CaCO_3$ per 100 lbs of seed) |

When delinting cotton seeds, a Final pH of greater than 3.5 is desired. The Final pH of delinted cotton seed impacts germination. Generally, the higher the pH of delinted cotton seed, the better the germination rate. Referring now to Table 2 above, the delinted cotton seed of Seed Example 3 has an Initial pH of 2.1 (above 2) while an Initial pH of the delinted cotton seed of Comparative Seed Example 3 is 1.7 (well below 2) Importantly, an Initial pH of greater than 2 means that a pre-neutralization step with $CaCO_3$ is not required, i.e, an Initial pH of greater than 2 means that an initial $CaCO_3$ treatment step, which is required in delinting processes known in the art, can be eliminated. Further, the delinted cotton seed of Seed Example 3 treated with 6 oz $CaCO_3$ per 100 lbs of seed has a pH of 3.9 (well above 3.5), while the pH of the delinted cotton seed of Comparative Seed Example 3 treated with 6 oz $CaCO_3$ per 100 lbs of seed is 1.8 (well below 3.5). Importantly, a Final pH greater than 3.5 is believed to provide higher germination rates and/or higher seed viability over time.

The delinted cotton seed of Seed Example 3 had a lower pH than the delinted cotton seed of Comparative Seed Example 3 at all three conditions set forth in Table 2 above. Notably, the delinted cotton seed of Seed Example 3 had an Initial pH of greater than 2 (with no $CaCO_3$ treatment) and required only 75% of the $CaCO_3$ treatment amount that was required for the delinted cotton seed of Comparative Seed Example 3. Reduction in a treatment amount of $CaCO_3$ used to increase the pH of delinted cotton seeds, and a higher Final pH of delinted cotton seed is desired. Unexpectedly, Seed Example 3 requires less $CaCO_3$ than Comparative Seed Example 3 and has a higher Final pH than Comparative Seed Example 3.

It is to be understood that the appended claims are not limited to express any particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present disclosure independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present disclosure, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The present disclosure has been described herein in an illustrative manner, and it is to be understood that the terminology which has been used is intended to be in the nature of words of description rather than of limitation. Many modifications and variations of the present disclosure are possible in light of the above teachings. The present disclosure may be practiced otherwise than as specifically described within the scope of the appended claims.

What is claimed is:

1. A method of delinting cotton seeds with an alkanesulfonic acid, said method comprising the steps of:
    applying the alkanesulfonic acid to surfaces of the linted cotton seeds;
    optionally heating the linted cotton seeds; and
    applying mechanical force to the surfaces of the linted cotton seeds.

2. A method as set forth in claim 1 wherein the alkanesulfonic acid is methanesulfonic acid (MSA).

3. A method as set forth in claim 1 wherein the step of heating the linted cotton seeds is conducted subsequent to the step of applying the alkanesulfonic acid, and the step of applying mechanical force is conducted subsequent to the step of heating.

4. A method as set forth in claim 1, wherein the step of applying mechanical force to the surfaces of the linted cotton seeds is further defined as mixing the linted cotton seeds in a rotating vessel.

5. A method as set forth in claim 1, wherein the step of applying the alkanesulfonic acid to the surface of linted cotton seeds is further defined as applying a composition comprising the alkanesulfonic acid, a surfactant, and water to the surface of a linted cotton seeds.

6. A method as set forth in claim 1, wherein a temperature of the linted cotton seeds does not exceed 65.6° C. (150° F.) during the step of heating the linted cotton seeds.

7. A method as set forth in claim 1, wherein the delinted cotton seeds have an Initial pH of greater than 2.

8. A method as set forth in claim 1, further comprising the step of applying calcium carbonate to the delinted cotton seeds.

9. A method as set forth in claim 8 wherein the delinted cotton seeds have a Final pH of greater than 3.5 when treated with equal to or less than 6 oz of $CaCO_3$ per 100 lbs of delinted cotton seeds.

10. A method as set forth in claim 1, wherein the delinted cotton seeds have a free fatty acid value (FFA) of from 0.05 to 0.70 g/100 g.

11. A method as set forth in claim 1, wherein the delinted cotton seeds have a germination rate at 27.5° C. (81.5° F.) of greater than 80%.

12. A method as set forth in claim 1 wherein the surfactant comprises an alcohol alkoxylate, and wherein the ratio of the alkanesulfonic acid to the surfactant, by weight, in the composition is from 120:1 to 4:1.

13. A method as set forth in anyone of claims 3-9 and 12, wherein the alkanesulfonic acid is methanesulfonic acid (MSA).

* * * * *